United States Patent [19]

Jorgensen et al.

[11] Patent Number: 5,182,279
[45] Date of Patent: Jan. 26, 1993

[54] BENZOTHIENOPYRAZINEDIONE COMPOUNDS AND THEIR PREPARATION AND USE

[75] Inventors: Anker S. Jorgensen, Copenhagen; Carsten E. Stidsen, Bagsværd; Peter Faarup, Værløse; Frederik C. Grønvald, Vedbæk; Flemming E. Nielsen, Virum, all of Denmark

[73] Assignee: Novo Nordisk A/S, Bagsvaerd, Denmark

[21] Appl. No.: 688,008

[22] Filed: Apr. 18, 1991

[30] Foreign Application Priority Data

Apr. 24, 1990 [DK] Denmark .............................. 1012/90

[51] Int. Cl.$^5$ .................. A61K 31/495; C07D 495/04; C07D 333/66; C07D 333/62
[52] U.S. Cl. .................................... 514/250; 544/345; 549/57
[58] Field of Search ......................... 514/250; 544/345

[56] References Cited

FOREIGN PATENT DOCUMENTS 0398283 11/1990 European Pat. Off. .

OTHER PUBLICATIONS

Cannizzo, Chem. Abs. 114, 143350 (Jul. 1990).

Cannizzo et al., Journal of Heterocyclic Chemistry, vol. 27, No. 7, pp. 2175-2179.

Primary Examiner—Mark L. Berch
Attorney, Agent, or Firm—Steve T. Zelson; Elias J. Lambiris

[57] ABSTRACT

Novel [1]benzothieno[2,3-b]pyrazine-2,3(1H,4H)-diones or tautomeric forms thereof of the general formula (I)

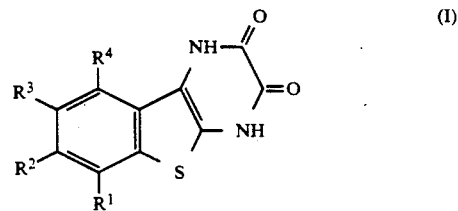

wherein $R^1$, $R^2$, $R^3$ and $R^4$ independently represent hydrogen, halogen, alkyl, alkoxy or trifluoromethyl.

The compounds are useful for treating a central nervous system ailment associated with the NMDA receptor-associated glycine site.

6 Claims, No Drawings

BENZOTHIENOPYRAZINEDIONE COMPOUNDS AND THEIR PREPARATION AND USE

The present invention relates to therapeutically active [1]benzothieno[2,3-b]pyrazine-2,3(1H,4H)-dione compounds or tautomeric forms thereof, a method of preparing the same, pharmaceutical compositions comprising the compounds, and a method of treating therewith.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 53, 321 (1985)) as well as anxiolytic activity (D.A. Bennett et al., Life Sci. 39, 2355 (1986)).

It has been suggested that accumulation of extracellular excitatory and neurotoxic amino acids, followed by hyperstimulation of neurons, may explain the neuronal degenerations seen in neurologicial diseases as Huntingtons chorea, Parkinsonism, epilepsia, senile dementia, and deficiencies of mental and motoric performance seen after conditions of brain ischemia, anoxia and hypoglycemia (E.G. McGeer et al., Nature, 263, 517 (1976) and R. Simon et al., Science, 226, 850 (1984)).

Excitatory amino acids exert their actions via specific receptors located postsynaptically or presynaptically. Such receptors are at present conveniently subdivided into three groups based on electrophysiological and neurochemical evidence: Quisqualate, kainate and NMDA (N-methyl-D-aspartate) receptors. L-glutamic acid and aspartic acid probably activate all the above types of excitatory amino acid receptors and possibly other types as well.

It was recently found that glycine was essential for NMDA receptor agonist induced responses in cultured neurons (J. W. Johnson et al., Nature 325, 529 (1987)). In contrast to glycine activated chloride conductance in spinal cord neurons, this response was insensitive to strychnine (D.W. Bonhaus et al., European J. Pharmacol. 142, 489 (1987)).

Glycine is believed to potentiate NMDA action through a modulatory site allosterically coupled to the NMDA ionophor complex (T. Honore et al., European J. Pharmacol. 172, 239 (1989)). D-serine and D-alanine exert a strong agonist activity on this site (J.B. Monahan et al., J. Neurochem. 53, 370 (1989)), whereas 1-aminocyclopropanecarboxylate (P. Skolnick et al., Life Sci. 45, 1647 (1989), V. Nadler et al., European J. Pharmacol. 157, 115 (1988), R. Trullas et al., Pharmacol. Biochem. Behav., 34, 313 (1989)) and D-cycloserine (W.F. Hood et al., Neurosci. Lett. 98, 91 /(1989)) act as partial agonists.

1-amino-cyclobutanecarboxylate (W.F. Hood et al., European J. Pharmacol. 161, 281 (1989)), 1-aminocyclopentanecarboxylate (L.D. Snell et al., European J. Pharmacol. 151, 165 (1988)), 3-amino-1-hydroxy-2-pyrrolidone (HA-966) (E.J. Fletcher et al., European J. Pharmacol. 151, 161 (1988)), 5-chloro-indole-2-carboxylate (J.E. Huettner, Science 243, 1611 (1989)) and 6-cyano-7-nitroquinoxaline 2,3-dione (CNQX) (R.A.J. Lester et al., Mol. Pharmacol. 35, 565 (1989)) are all weak antagonists, whereas 7-chlorokynurenic acid (7-Cl-Kyn) (R. Sircar et al., Brain Res. 504, 325 (1989)) and 6,7-dichloro-3-hydroxy-quinoxalin-2-carboxylate (M. Kessler et al., Brain Res. 489, 377 (1989)) are quite strong antagonists of glycine at the glycine site. However, all of the above reported compounds act nonselectively at this site in so far as they have higher or equal affinity for other targets.

We have now discovered a series of benzothieno[2,3-b]pyrazine-2,3(1H,4H)-dione derivatives which appears to be potent and selective antagonists at the glycine binding site on the NMDA receptor complex.

The present invention accordingly provides compounds of the formula (I) or tautomeric forms thereof:

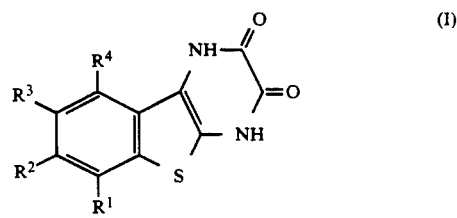

(I)

wherein $R^1$, $R^2$, $R^3$ and $R^4$ independently represent hydrogen, halogen, $C_{1-6}$ alkyl, $C_{1-6}$ alkoxy or trifluoromethyl, acceptable salts thereof.

The invention also relates to a method of preparing the above-mentioned compounds. This method involves an intermediate (VII) which may be prepared by the following methods:

a) alkylating a compound of the formula (II)

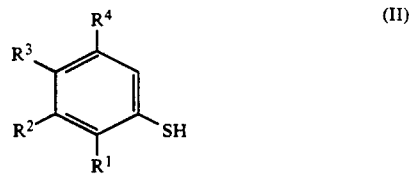

(II)

wherein $R^1$–$R^4$ independently represent H, halogen or trifluoromethyl, with bromoacetaldehyde dimethyl acetal, to form a compound of formula (III)

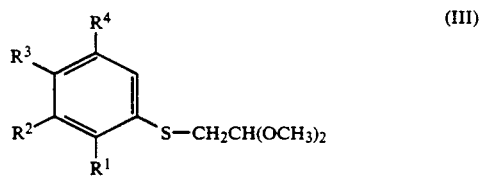

(III)

wherein $R^1$–$R^4$ have the meaning defined for formula (II).

Ringclosure of a compound of formula (III) under acidic conditions in the presence of an inert solvent, preferably polyphosphoric acid and chlorobenzene as solvent, to form a compound of formula (IV)

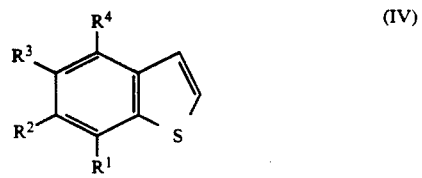

(IV)

wherein $R^1$–$R^4$ have the meaning as defined for formula (II). (For similar type of reaction see, for example, P.A.

Plé and L. J. Marnett, J. Heterocyclic Chem., 25, 1271 (1988)).

Brominating a compound of formula (IV) to form a compound of formula (V)

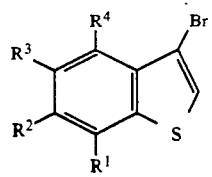

wherein $R^1$-$R^4$ have the meaning as defined for formula (II). (For similar type of reaction see, for example, G. Van Zyl et al., Can. J. Chem., 44, 2283(1966)).

Nitrating a compound of formula (V) to form a compound of the formula (VI)

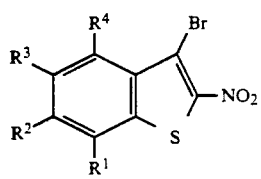

wherein $R_1$-$R^4$ have the meaning as defined for formula (II).

Reacting a compound of formula (VI) with ammonia in a suitable solvent, e.g. diglyme or 2-methoxyethanol to form a compound of formula (VII)

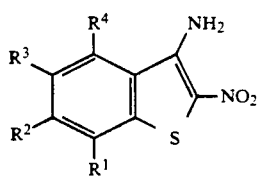

wherein $R^1$-$R^4$ have the meaning as defined for formula (II). (For similar type of reaction see, for example, G. Van Zyl et al., Can. J. Chem, 44, 2283 (1966)).

b) reacting a compound of formula (VIII) (methods for preparation of compounds of type (VIII), see for example, N.V. Harris et al., J. Med. Chem., 33, 434 (1990))

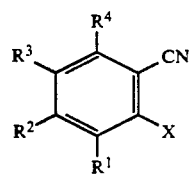

wherein X is a leaving group preferably nitra or halogen and $R^1$-$R^4$ have the meaning as defined for formula (I), with sodium sulphide in aqueous DMF or mercaptopropionitrile in alkaline solution followed by addition of bromonitromethane (through an intermediary o-cyanobenzenethiolate), to form a compound of formula (VII) wherein $R^1$-$R^4$ have the meaning as defined for formula (I). (For similar type of reaction cf. J. R. Beck, J. Org. Chem., 37, 3224 (1972), J. R. Beck and J. A. Yahner, J. Org. Chem., 39, 3441 (1974)).

c) Reacting a compound of formula (IX) (methods for preparation of compounds of type (IX), see for example L.K.A. Rahman and R.M. Scrowston, J. Chem. Soc. Perkin Trans. I, 2973 (1983)) R4

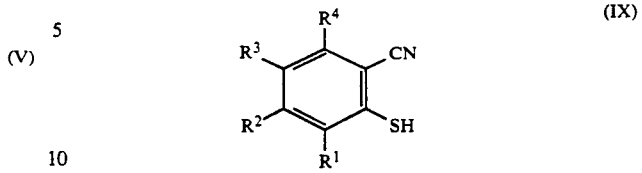

wherein $R^1$-$R^4$ have the meaning as defined (I), with bromonitromethan in the presence of a base (analoguous to the method described by D.E.L. Carrington et al., J. Chem. Soc. (C), 3903 (1971)) to form a compound pound of formula (VII) wherein $R^1$-$R^4$ have the meaning as defined for formula (I).

The intermediate (VII) may be reacted to (I) by the following methods:

d) reacting a compound of formula (VII) with ethyl oxalylchloride in a suitable solvent in the precense of a base; e.g. THF and pyridine with 4-dimethylaminopyridine as co-catalyst, to form a compound of formula (X)

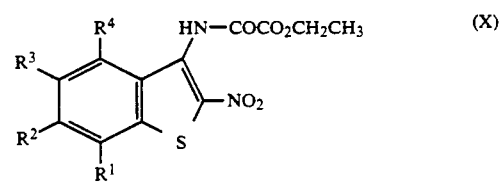

wherein $R^1$-$R^4$ have the meaning as defined for formula (I).

Reducing a compound of the formula (X) with e.g. zinc in 80% acetic acid or Tin(II)chloride in hydrochloric acid, to form a compound of formula (I).

e) Reducing a compound of formula (VII) in the presence of a catalyst and hydrochloric acid to form a compound of the formula (XI)

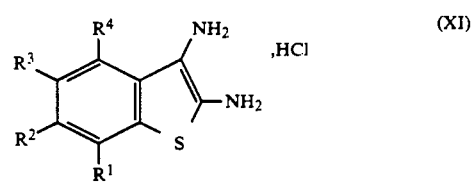

wherein $R^1$-$R^4$ have the meaning set forth above.

Reacting a compound of formula (XI) with ethyl oxalylchloride in THF under basic conditions to form a compound of formula (XII)

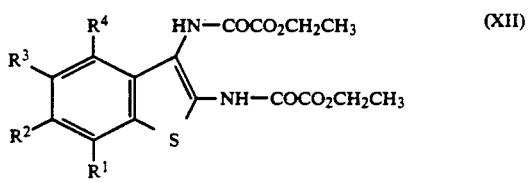

wherein $R^1$-$R^4$ have the meaning set forth above.

Reacting a compound of formula (XII) with a mineral acid; e.g. hydrochloric acid to form a compound of formula (I).

The affinity of a substance for one or more of the different types of excitatory amino acid receptors may be studied in simple radioligand binding experiments. In essense, the method involves incubation of a particular selected radiolabelled ligand and the particular specific substance to be investigated with brain homogenates which contain the receptor. Measurement of receptor occupancy is made by determination of the radioactivity bound to the homogenate and subtraction of nonspecific binding.

The influence of glutamic acid analogues on secondary effects of glutamate receptor interactions, such as on c-GMP formation and on channel opening, may be studied in vitro by using brain slices or homogenates. Such experiments will provide information as to the efficacies (agonist/antagonist) of the test substances.

It has now been found that the heterocyclic compounds of the invention have affinity for the glycine site of the NMDA receptor complex and are antagonists in connection with this type of receptors. This will make them useful in the treatment of any of the numerous indications caused by hyperactivity of excitatory amino acids.

The glycine site binding activity of these compounds of the present invention can be illustrated by determining their capability for displacing radioactively labelled glycine from the glycine site.

The displacement activity of the compounds may be shown by determining the $IC_{50}$ value which represents the concentration ($\mu M$) which causes a displacement of 50% of the specific binding of [$^3H$]-glycine.

The glycine antagonistic properties of the compounds is demonstrated by their capability to antagonize glycine enhanced binding of the non-competitive NMDA antagonist [$^3H$]-MK-801 to brain homogenates. The glycine antagonism is measured by determining the $K_i$ value which represents the dissociation constant ($\mu M$) of the receptor-antagonist complex.

The NMDA antagonistic properties of the compounds is illustrated by determining their capability to antagonize NMDA stimulated [$^3H$]-GABA release from cultured mouse cortex neurons. The NMDA antagonistic activity of the compounds may be shown by determining the $IC_{50}$ value, which represents the concentration ($\mu M$) which inhibits 50% of NMDA induced [$^3H$]-GABA release.

[$^3H$]-glycine binding (Test 1)

1 ml of thawed rat cerebral cortical membrane homogenate in HEPES-Tris (5 mM) and $MgCl_2$(1 mM) pH 7.1 were incubated at 0° C. for 10 min. with 25 $\mu l$ (final concentration) and the test compound and buffer. Non-specific binding was determined by incubating with D-serine (1 mM final concentration). The binding reaction was terminated by centrifugation at 15,000 ×g at 4° C. followed by washing of the pellet with three times 3 ml of ice-cold buffer. Bound radioactivity was measured by scintillation counting. $IC_{50}$ was determined by Hill analysis of at least four concentrations of test compound.

Antagonism enhanced [$^3H$]-MK-801 binding (Test 2)

1 ml of thawed and extensively washed rat cerebral membrane homogenate in HEPES-NaOH (20 mM) pH 7.40 were incubated at 23° C. for 60 min. with 25$\mu l$[$^3H$]-MK-801 (1 nM final concentration), 25 $\mu l$ glutamate (300 nM final concentration), test compound in concentrations corresponding to 0, 0.5, 2 and 5 times the $IC_{50}$ value from the [$^3H$]-glycine binding assay (test 1) for each concentration of glycine (10; 100; 1,000; 10,000 and 100,000 nM final concentration). The binding reaction was terminated by adding 5 ml of ice-cold buffer followed by rapid filtration through Whatman GF/C glass fiber filters and 5 ml wash with ice-cold buffer. Bound radioactivity was measured by scintillation counting. $K_i$ values were determined by Schild analysis of the data using $$\log(\text{dosis ration} - 1) = \log[\text{Inhibitor}] - \log(K_i)$$

Inhibition of NMDA stimulated [$^3H$]-GABA release from cultured mouse cerebral cortex interneurons (Test 3)

Release experiments are performed using the model described by Drejer et al. (Life Sci. 38, 2077 (1986)). To cerebral cortex interneurons cultured in petri dishes (30 mm) are added 100 $\mu g/ml$ 3-vinyl-GABA one hour before the experiment in order to inhibit degradation of GABA in the neurons. 30 min. before the experiment 5 $\mu Ci$ [$^3H$]-GABA added to each culture and after this preloading period the cells are washed twice with HEPES buffered saline (HBS) containing 10 mM HEPES, 135 mM NaCl, 5 mM KCl, 0.6 mM $MgSO_4$, 1.0 mM $CaCl_2$ and 6 mM D-glucose; pH 7 and placed in a superfusion system. This system consists of a peristaltic pump continuously delivering thermostated 37° C. superfusion medium from a reservoir to the top of a slightly tilted petri dish. The cell monolayer at the bottom of the dish is covered with a piece of nylon mesh to facilitate dispersion of medium over the cell layer. The medium is continuously collected from the lower part of the dish and delivered to a fraction collector. Initially, the cells are superfused with HBS for 15 min. (flow rate 2 ml/min.). Then cells are stimulated for 30 sec. every 4 min. by changing the superfusion medium from HBS to a corresponding medium containing NMDA and antagonist according to the following scheme:

Stimulation no. 1: 3 $\mu g/ml$ NMDA
Stimulation no. 2: 3 $\mu g/ml$ NMDA +0.3 $\mu g/ml$ antagonist
Stimulation no. 3: 3 $\mu g/ml$ NMDA +3.0 $\mu g/ml$ antagonist The release of [$^3H$]-GABA in the presence of NMDA is corrected for the mean basal release before and after stimulation. The stimulated release in the presence of antagonist is expressed relative to the stimulated release by NMDA alone and the $IC_{50}$ value is calculated.

Test results obtained by testing some compounds employed in the present invention will appear from the following table 1.

TABLE 1

| Compound of Example | Test 1 $IC_{50}$ $\mu M$ | Test 2 $K_i$ $\mu M$ | Test 3 $IC_{50}$ $\mu M$ |
|---|---|---|---|
| 1 | 0.052 | 0.008 | 0.039 |
| 2 | 0.056 | 0.040 | 0.011 |
| 3 | 0.284 | 0.208 | 0.085 |
| 4 | 0.069 | 0.018 | ND |
| 5 | 6.000 | ND | ND |
| 7 | 0.312 | ND | 0.068 |
| 8 | 1.000 | ND | 0.112 |
| 9 | 7.000 | ND | ND |
| 10 | 10.800 | ND | ND |
| 11 | 15.000 | ND | ND |
| 12 | 0.180 | 0.041 | ND |

TABLE 1-continued

| Compound of Example | Test 1 IC$_{50}$ μM | Test 2 K$_i$ μM | Test 3 IC$_{50}$ μM |
|---|---|---|---|
| 13 | 0.262 | ND | ND |
| 14 | 0.540 | ND | ND |
| 7-Cl-Kyn* | 1.4 | 0.71 | 1.3 |
| HA-966* | 13 | 16 | 25 |

ND: Not determined
*) Reference compounds, see above.

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) to two hundred (200) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| | |
|---|---|
| Active compound | 2.0 mg |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of effect as glycin antagonists, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, hypnotic, nootropic and anxiolytic activities along with a low toxicity, together presenting a most favorable therapeutic index. The compounds of the invention may accordingly be administered to a subject, e.g., a living mammal body, including a human, in need of the same for the treatment, alleviation, amelioration, or elimination of an indication, associated with the central nervous system and the socalled NMDA receptors, which requires such psychopharmaceutical treatment, e.g., especially convulsion, anxietyepilepsy and ischemia if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically- acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their NMDA receptor affinity. Suitable dosage ranges are 1-200 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples, which may not be construed as limiting:

EXAMPLE 1

8-Fluoro[1]benzothieno[2,3-b]pyrazine-2,3(1H,4H)-dione

Method A

5-Fluorobenzo[b]thiophene

Sodium (18.08 g, 786 mmol) was dissolved in dry ethanol (600 ml) and 4-fluorothiophenol (97 g, 749 mmol) was added slowly. Sodium iodide (22.45 g, 150 mmol) was then added to the stirred mixture followed by bromoacetaldehyde dimethyl acetal (132.86 g, 786 mmol). The mixture was boiled under reflux with stirring for 3 hours and left with stirring for 16 hours at room temperature. The solvent was partly evaporated (500 ml of distillate collected) and the residue was poured into ice water. The viscous oil which separated was extracted with ethyl acetate (3×300 ml), the extract was washed with water (150 ml) and dried (MgSO$_4$). After removal of ethyl acetate 161 g (99%) of crude (4-fluorophenylthio)- acetaldehyde dimethyl acetal was obtained and used in the next step without further purification. $^1$H-NMR (CDCl$_3$): δ3.00 (d, 2H, J=5Hz), 3.27 (s, 6H), 4.45 (t, 1H, J=5Hz), 6.80-7.50 (m, 4H).

Anhydrous chlorobenzene (1500 ml) was placed in a 3 liter 3-necked flask equipped with a condenser and a mechanical stirrer. The apparatus was flushed with nitrogen and about 495 grams of polyphosphoric acid (PPA) was added. The mixture was brought to gentle reflux and 161 g (0.74 mol) of crude (4-fluorophenylthio)- acetaldehyde dimethyl acetal was added during 2.5 hours and the solution was further refluxed for 19 hours. The reaction mixture was allowed to cool to ambient temperature and the organic phase was separated from the PPA. Residual PPA was decomposed with water and the resulting aqueous phase was extracted with toluene (2×150 ml). The combined organic phases was dried over MgSO$_4$ and the solvents evaporated. The residue was fractionated to give 62.4 g (55%) of 5-fluorobenzothiophene which had b.p. 76°-77° C./ 4.5 mm Hg and m.p. 21°-22° C. $^1$H-NMR (CDCl$_3$)δ7.00 (ddd, 1H), 7.20 (d, 1H, J =5.5Hz), 7.36 (dd,1H), 7.47 (d, 1H, J =5.5 Hz), 7.70 (dd,1H).

Method B

3-Bromo-5-fluorobenzo[b]thiophene

A solution of 5-fluorobenzo[b]thiophene (99 g, 650 mmol)

400 ml of CCl$_4$ was stirred maintaining the temperature at 10°-15° C. A cooled solution (15°-20° C.) of bromine (103 g, 644 mmol) in 120 ml of CCl$_4$ was added at such a rate that the temperature was kept below 20° C. When the addition was complete stirring was continued for 4 days at 15°-20° C. The slightly brown reaction mixture was decolourized by addition of 2M Na$_2$S$_2$O$_3$ (2 ml) and ice water (150 ml) and stirring for 1 hour. The organic phase was separated and the aqueous phase was extracted with 300 ml of CCl$_4$. The combined organic phases was washed with water (2×100 ml), dried over MgSO$_4$ and the solvent was stripped off to give 145.8 g (98%) of crude 3-bromo-5-fluorobenzo[b]thiophene, which had m.p. 79°-80° C. when recrystallized from alcohol. $^1$H-NMR (DMSO-d$_6$):δ7.40 (ddd, 1H, J=8.4 Hz, J=9,4 Hz, J=2.4), 7.53 (dd, 1H, J=9.4 Hz, J =2.4 Hz), 8.17 (m, 2H).

Method C

3-Bromo-5-fluoro-2-nitrobenzo[b]thiophene

A solution of 5.12 ml of fuming nitric acid and 4.5 ml of acetic acid was added dropwise, with stirring, to a cooled (5°-10° C.) mixture of 3-bromo-5-fluorobenzo[b]thiophene (5.35 g, 23.15 mmol) and 28.5 ml of acetic anhydride. The reaction mixture was stirred for 2 hours and poured onto ice water (350 ml) and extracted with CH$_2$Cl$_2$ (4×50 ml). The organic phases were combined, washed with water and dried over MgSO$_4$. The solvent was evaporated and the residue was recrystallized from 90% ethanol to yield 1.7 g (26%) of 3-bromo-5-fluoro-2-nitrobenzo[b]thiophene. M.p. 129°-130° C. $^1$H-NMR(CDCl$_3$): δ7.40 (ddd, 1H), 7.68 (ddd, 1H), 7.78 (dd, 1H).

Method D

3-Amino-5-fluoro-2-nitrobenzo[b]thiophene

A solution of 3-bromo-5-fluoro-2-nitrobenzo[b]thiophene (1.51 g, 5.47 mmol) in 10 ml of 2-methoxyethanol was placed in a steel bomb. 2-Methoxyethanol (15 ml) was saturated with ammonia at 0° C. and the obtained solution was added to the steel bomb. The bomb was sealed, heated to 90° C. for 16 hours and cooled in an ice bath. After ammonia gas was sufficiently released, the reaction mixture was poured onto ice water (250 ml). The precipitate was filtered off, washed with water and dried. Yield 1.06 g (91%) of 3-amino-5-fluoro-2-nitrobenzo[b]thiophene.

M.p. 231°-232° C. (dec.). $^1$H-NMR (DMSO-d$_6$): δ7.57 (ddd, 1H, J=8.4 Hz, J=9.4 Hz, J=2.4 Hz), 7.95 (dd, 1H, J=8.4 Hz J=9.4 Hz), 8.23 (dd, 1H, J=10 Hz, J=2.4 Hz), 8.83 (br. s, 2H).

Method E

Ethyl N-(5-fluoro-2-nitrobenzo[b]thien-3-yl)oxamate

3-Amino-5-fluoro-2-nitrobenzo[b]thiophene (0.7 g, 3.3 mmol) was dissolved in 10 ml of dry pyridine. The mixture was cooled to −10° C. and flushed with a stream of dry nitrogen. 4-Dimethylaminopyridine (40.3 mg, 0.33 mmol) was added followed by dropwise addition of a solution of ethyl oxalylchloride (0.565 ml, 4.95 mmol) in 3.3 ml of dry THF. The reaction mixture was stirred for 5 hours at −10° C., left overnight at room temperature, and then poured onto ice water. The precipitate was filtered off, washed with water, and dried to yield 0.98 g (95%) of pure Ethyl N-(5-fluoro-2-nitrobenzo[b]thien-3-yl)oxamate. M.p. 129°-31° C. $^1$H-NMR (DMSO-d$_6$: δ1.36 (t, 3H, J =7.5 Hz), 4.36 (q, 2H, J 7.5 Hz), 7.60 (ddd, 1H), 7.86 (dd, 1H), 8.16 (dd, 1H), 11.36 (br. s, 1H).

Method F

8-Fluoro[1][2,3(1H,4H)-dione

A suspension of ethyl N-(5-fluoro-2-nitrobenzo[b]-thien3-yl)oxamate (0.8 g, 2.55 mmol) in 40 ml of 80% acetic acid was stirred and flushed with a stream of dry nitrogen. Zinc (1.67 g, 25.54 mmol) was added and the mixture was stirred at room temperature for 16 hours, and 50 ml of water was added. Stirring was continued for 2 days, the precipitate was filtered off, and dissolved in 55 ml of boiling glacial acetic acid. Activated carbon was added, and after filtration the filtrate was evaporated to about half the volume. The mixture was boiled and water (20 ml) was added dropwise until incipient turbidity. After cooling to room temperature, the precipitate was filtered off, washed with water and dried to yield 0.43 g (71%) of th title compound. M.p. >340° C. 1H-NMR (DMSO-d$_6$): δ7.20 (ddd, 1H) 7.88 (dd, 1H), 7.98 (dd, 1H), 12.46 (s, 1H), 12.50 (s, 1H).

Analysis: Calculated for C$_{10}$H$_5$N$_2$O: C., 47.24; H, 2.78; N, 11.02; S, 12.61%. Found: C, 47.34; H, 2.74; N, 10.89; S, 12.66%.

EXAMPLE 2

8-Chloro[1]benzothieno[2,3,-b]pyrazine-2,3(1H,4H)-dione

5-Chlorobenzo[b]thiophene (21.65 g, 103 mmol) (P.A. Ple L. J. Marnett, J. Heterocyclic Chem., 25, 1271 (1988)) was brominated following the procedure outlined in example 1 (Method B). Yield 12.2 g (48%) of 3-bromo-5-chlorobenzo[b]thiopene. M.p. 82° C. $^1$H-

NMR (CDCl$_3$): δ7.34 (dd, 1H), 7.50 (s, 1H), 7.73 (d, 1H), 7.80 (d, 1H).

Nitration of 3-bromo-5-chlorobenzo[b]thiophene (12.10 g, 49 mmol) was performed following the procedure outlined in example 1 (Method C). The reaction mixture was poured onto ice water to give a precipitate, which was filtered off, washed with diluted acetic acid and dried. Yield 4.42 g (31%) of 3-bromo-5-chloro-2-nitrobenzo[b]thiophene. M.p. 176°-78° C. $^1$H-NMR(CDCl$_3$): δ7.57 (dd, 1H), 7.74 (d, 1H), 8.00 (dd, 1H).

Reaction of 3-bromo-5-chloro-2-nitrobenzo[b]thiophene (3.55 g, 12.14 mmol) with ammonia was performed following the procedure outlined in example 1 (Method D). Yield 2.7 g (98%) of 3-amino-5-chloro-2-nitrobenzo[b]thiophene. M.p. 272°-274° C. (dec.) $^1$H-NMR (CDCl3 DMSO-d$_6$, 4:3): δ7.52 (dd, 1H), 7.65 (d, 1H), 8.44 (dd, 1H), 8.62 (br. s, 2H).

Ethoxalylation of 3-amino-5-chloro-2-nitrobenzo[b]thiophene (0.75 g, 3.06 mmol) was performed following the procedure outlined in example 1 (Method E). Yield 0.99 g (98%) of ethyl N-(5-chloro-2-nitrobenzo[b]thien-3-yl)oxamate. M.p. 126°-128° C. $^1$H-NMR (DMSO-d$_6$) δ1.38 (t, 3H, J=7.5 Hz), 4.38 (q, 2H, J =7.5 Hz), 7.74 (dd, 1H), 8.16 (m, 2H), 11.46 (br. s, 1H).

Reduction of ethyl N-(5-chloro-2-nitrobenzo[b]thien-3yl)oxamate (0.9 g, 2.74 mmol) was performed following the procedure outlined in example 1 (Method F) to yield 0.43 g (62%) of the title compound. M.p. >340° C. $^1$H-NMR (DMSO-d$_6$) δ7.30 (dd, 1H, J =8 Hz, J=1.5 Hz), 7.94 (d, 1H, J =8 Hz), 8.11 (d, 1H, J=1.5 Hz), 12.50 (br.s, 2H).

Analysis: Calculated for C$_{10}$H$_5$N$_2$ClO$_2$S. H$_2$O: C, 44.37; H, 2.61; N, 10.35; Cl, 13.10; S, 11.84%. Found: C, 44.33; H, 2.64; N, 10.13; Cl, 13.29; S, 11.82%.

EXAMPLE 3

[Benzothieno[2,3-b]pyrazine-2,3(1H,4H)-dione

Method G 2,3-diaminobenzo[b]thiophene hydrochloride

Fuming hydrochloric acid (1.92 ml, 24 mmol) was added to a suspension of 3-amino-2-nitrobenzo[b]thiophene (4.66 g, 24 mmol) (G. Van Zyl et al., Can. J. Chem., 44, 2283 (1966)) in 500 ml of 96% ethanol, and the mixture was hydrogenated in a Parr hydrogenation apparatus for 7 h at 40 psi and room temperature in the presence of 1 g of 5% palladium on carbon. The catalyst was filtered off under nitrogen, and the filtrate was evaporated to dryness to give 4.89 g (100%) of 2,3-diaminobenzo[b]thiophene hydrochloride, which was used in the next step without further purification.

Method H 2,3-Bis(ethoxalylamino)benzo[b]thiophene:

Crude 2,3-diaminobenzo[b]thiophene hydrochloride (4.8 g, 24 mmol) was partially dissolved in 200 ml of dry tetrahydrofuran, and a stream of dry nitrogen was bubbled through the mixture. Then dry triethylamine (10.0 ml, 72 mmol) was added with stirring on an ice bath, followed by the dropwise addition of ethyl oxalylchloride (5.4 ml, 48 mmol). The mixture was stirred at O°C for 1 h, and then refluxed for 30 min. After cooling on an ice bath, the triethylamine hydrochloride was filtered off, and the filtrate was evaporated to dryness to give a dark oil. Trituration with ether afforded 7.1 g (81%) of almost pure 2,3-bis(ethoxalylamino)benzo[b]thiophene; m.p. 130°- C.; H-NMR (CDCl$_3$): δ1.40 (t, J7 Hz, 6H, 2 CH$_3$), 4.36 (q, J=7 Hz, 2H, CH$_2$), 4.39 (q, J=7 Hz, 2H, CH$_2$), 7.15-7.87 (m, 4H, ArH), 9.27 (broad s, 1H, NH), 11.25 (broad s, 1H, NH).

Method I

[1]Benzothieno[2,3-b]pyrazine-2,3(1H,4H)-dione

A suspension of 2,3-bis(ethoxalylamino)benzo[b]thiophene (5.47 g, 15 mmol) in 250 ml of 4 N hydrochloric acid was heated to reflux for 2 h. Then the mixture was cooled on an ice bath, and filtered. The crude product was washed with water and recrystallized from a mixture of ethanol, DMF and water with decolorizing charcoal. The recrystallized solid was filtered off, washed with ethanol and ether, and dried for 1 h at 100° C to give 2.2 g (62%) of the pure title compound as a monohydrate; m.p. 377.6° C. DSC); 1R (KBr): 3200-2500, 1670 cm$^{-1}$; $^1$H-NMR (DMSO-d$_6$): δ 3.3 (broad s, 2H, H$_2$O); 7.1-7.6 (m, 2H, ArH), 7.8-8.1 (m, 2H, ArH), 11.9-13.6 (broad, 2H, 2NH); MS (m/e): 218 (M+, 100%).

Analysis: Calculated for C$_{10}$H$_6$N$_2$O$_2$S. H$_2$O: C, 50.84; H, 3.41; N, 11.86%. Found: C, 50.86; H, 3.39; N, 11.77%.

EXAMPLE 4

8-Bromo[1]benzothieno[2,3-b]pyrazine-2,3(1H,4H)-dione

5-Bromobenzo[b]thiophene(5.97 g, 28 mmol) (P.A. Ple and L. J. Marnett, J. Heterocyclic Chem., 25, 1271 (1988)) was brominated following the procedure outlined in example 1 (Method B). Yield 7.55 g (92%) of 3,5-dibromobenzo[b]thiophene. M.p. 95°-97° C. 7.52 (dd, 1H), 7.72 (d, 1H), 7.79 (d, 1H).

Nitration of 3,5-dibromobenzo[b]thiophene (7.0 g, 24 mmol) was performed for 1 h following the procedure of example 1 (Method C). The precipitate formed during the reaction was filtered off, washed with dilute acetic acid and dried. Yield 2.2 g (27%) of 3,5-dibromo-2-nitrobenzoδthiophene. M.p. 193°95° C. $^1$H-NMR(CDCl$_3$): δ7.75 (m, 2H), 8.20 (dd, 1H).

A mixture of 3,5-dibromo-2-nitrobenzo[b]thiophene (2.02 g, 6 mmol), ethanol (100 ml) and 25% ammonia solution (6 ml) was heated at 70° C. for 24 h in a stoppered flask. The reaction mixture was cooled and poured into ice-water.

The precipitate was filtered off, washed with water and dried. Yield 1.48 g (90%) of 3-amino-5-bromo-2-nitrobenzo[b]thiophene. M.p. 282°-84° C. $^1$H-NMR (DMSO-d$_6$): δ7.83 (dd, 1H), 7.88 (d, 1H), 8.65 (d, 1H), 8.86 (br. s, 2H).

Ethoxalylation of 3-amino-5-bromo-2-nitrobenzo[b]thiophene (1.37 g, 5 mmol) was performed following the procedure outlined in example 1 (Method E). The reaction mixture was poured onto ice and extracted with dichloromethane. The extracts were washed with water, decolorized with activated carbon and dried (MgSO$_4$). The solvent was removed in vacuo to afford 1.78 g (95%) of ethyl N-(5-bromo-2-nitrobenzo[b]thien-3-yl)oxamate. M.p. 157°-160 ° C. $^1$H-NMR (DMSO-d ): δ1.36 (t, 3H), 4.34 (q, 2H), 7.87 (dd, 1H), 8.15 (d, 1H), 8.37 (d, 1H), 11,50 (s, 1H).

Reduction of ethyl N-(5-bromo-2-nitrobenzo[b]thien-3-yl)oxamate (1.49 g, 4 mmol) was performed following the procedure outlined in example 1 (Method F) to yield 0.6 g (50%) of the title compound. M.p. >320° C.

1H-NMR (DMSOd$_6$): δ7.42 (dd, 1H), 7.92 (d, 1H), 8.38 (dd, IH), 12.45 (br. s, 2H).

Analysis: Calculated for : C$_{10}$H$_5$BrN$_2$O$_2$S: C, 40.42; H, 1.70; N, 9.43; Br, 26.89; S, 10.79%. Found: C, 40.39; H, 1.67; N, 9.41; Br, 27.54; S, 10.95%.

EXAMPLE 5

7-Chloro[1]benzothieno[2,3-b]pyrazine-2,3(1H,4H)-dione

Method J 3-Amino-6-chloro-2-nitrobenzo[b]thiophene

A solution of 4-chloro-2-nitrobenzonitrile (2.19 g, 12 mmol) (EP 110,559; cf. Chem. Abstr., 101 130431 f (1984)) in 40 ml of DMF was stirred under cooling (ice bath), and a solution of sodium sulfide nonahydrate (3.47 g, 14.4 mmol) in 8 ml of water was added dropwise. When the addition was complete (0.5 h) the mixture was stirred for 15 min. and bromonitromethane (2.02 g, 14.4 mmol) was added dropwise. The ice bath was removed and stirring was continued for 16 h. The reaction mixture was poured into icewater and the yellow precipitate was filtered off and dried to afford 1.05 g (38%) of 3-amino-6-chloro-2-nitrobenzo[b]thiophene M.p. 243°-245° C. $^1$H-NMR (DMSO-d$_{67}$): δ 7.55 (dd, 1H), 8.11 (d, 1H), 8.36 (d, 1H), 8.97 (br. s, 2H).

Ethoxalylation of 3-amino-6-chloro-2-nitrobenzo[b]thiophene (0.91 g, 4 mmol) was performed following the procedure outlined in example 1 (Method E). The reaction mixture was poured into water and extracted with dichloromethane. The organic phases were collected, washed with water, dried (MgSO$_4$) and evaporated in vacuo. Yield 0.63 g (48%) of ethyl N-(6-chloro-2-nitrobenzo[b]thien-3-yl)oxamate. M.p. 139°-141° C. $^1$H-NMR (CDC13): δ7.47 (dd, 1H), 7.79 (d, 1H), 8.23 (d, 1H), 11.24 (s, 1H).

Reduction of N-(6-chloro-2-nitrobenzo[b]thien-3-yl)oxamate was performed following the procedure outlined in example 1 (Method F) to give the title compound. M.p. >300° C. H-NMR (DMSO-d$_6$) δ7.50 (dd, 1H), 8.03 (d, 1H), 8.13 (d, 1H), 12.42 (s, 1H), 12.58 (s, 1H).

EXAMPLE 6

9-Chloro-[1]benzothieno[2,3-b]pyrazine-2,3(lH,4H)-dione

6-Chloro-2-nitrobenzonitrile (19.39 g, 104 mmol) was reacted with sodium sulfide and bromonitromethane following the procedure outlined in example 5 (Method J). Yield 7 g (29%) of crude 3-amino-4-chloro-2-nitrobenzo[b]thiophene. M.p. 174°-75° C. (2-propanol). $^1$H-NMR (CDCl$_3$): δ7.37 (d, 1H), 7,47 (t, 1H), 7.60 (d, 1H), 8.30 (br. s, 2H).

Ethoxalylation of 3-amino-4-chloro-2-nitrobenzo[b]thiophene (0.55 g, 2.4 mmol) was performed following the procedure outlined in example 1 (Method E) to afford 0.71 g (90%) of ethyl N-(4-chloro-2-nitrobenzo[b]thien-3-yl)oxamate. $^1$H-NMR (CDCl$_3$): δ1.46 (t, 3H), 4.46 (q, 2H), 7.52 (m, 2H), 7.75 (d, 1H), 10.10 (br. s, 1H).

Reduction of N-(4-chloro-2-nitrobenzo[b]thien-3-yl)oxamate was performed following th procedure outlined in example 1 (Method F) to give the title compound. $^1$H-NMR (DMSO-d$_6$): δ7.33 (t, 1H), 7.48 (d, 1H), 7.96 (d, 1H), 12.60 (br. s, 2H).

Analysis: Calculated for C$_{10}$H$_5$N$_2$C1O$_2$S. 1.25 H$_2$O: C, 43.64; H, 2.74; N, 10.18; Cl, 12.88%. Found: C, 43.62; H, 2.50; N, 9.70; Cl, 12.72%.

EXAMPLE 7

6,8-Dichloro[1]benzothieno[2,3-b]pyrazine-2,3(1H,4H)dione

A mixture of 2,3,5-trichlorobenzaldehyde (19.8 g, 94 mmol), hydroxylamine hydrochloride (9.8 g, 141 mmol), sodium formate (13.4 g, 197 mmol), and formic acid (200 ml) was heated under reflux for 6 h. The reaction mixture was poured into ice-water, and the precipitate was filtered off and dried. Yield 19 g (98%) of 2,3,5-trichlorobenzonitrile. M.p. 77°-78° C. $^1$H-NMR (DMSO-d$_6$): δ8.26 (d, 1H), 8.28 (d, 1H).

3-Amino-5,7-dichloro-2-nitrobenzo[b]thiophene

Method K 2,3,5-Trichlorobenzonitrile (9.7 g, 47 mmol) and 3-mercaptopropionitrile (4.9 g, 56 mmol) (L. Bauer, T.L. Welsh, J. Org. Chem., 1443 (1961)) was dissolved in 130 ml of DMF. The mixture was stirred and cooled to 0° C., flushed with a stream of nitrogen, and 25% potassium hydroxide (20 ml) was added dropwise. When the addition was complete the mixture was stirred for 0.5 h and bromonitromethane (3.92 ml, 56 mmol) was added dropwise. The ice bath was removed and the mixture was stirred for a further 16 h. The mixture was poured into ice-water and the precipitate was isolated, washed with water and dried to afford 10.6 g (86%) of 3-amino-5,7-dichloro-2-nitrobenzo[b]-thiophene M.p. 290°-92° C. $^1$H-NMR (DMSO-d$_6$): 8.02 (d, 1H), 8.54 (d, 1H), 9.00 (br. s, 1H).

Ethoxalylation of 3-amino-5,7-dichloro-2-nitrobenzo[b]thiophene (2.63 g, 10 mmol) was performed following the procedure outlined in example 1 (Method E) to afford 3.4 g (93%) of ethyl N-(5,7-dichloro-2-nitrobenzo[b]thien3-yl)oxamate. M.p. 177°-80° C. 1H-NMR (DMSO-d$_6$): δ1.38 (t, 3H), 4.39 (q, 2H), 8.11 (d, 1H), 8.27 (d, 1H), 11.62 (br. s, 1H).

Reduction of ethyl N-(5,7-dichloro-2-nitrobenzo[b]thien3-yl)oxamate (1.6 g, 4.4 mmol) was performed following the procedure outlined in example 1 (Method F) to yield 0.58 g (43%) of the title compound. M.p. >300° C. $^1$HNMR (DMSO-d$_6$): δ7.57 (d, 1H), 8.13 (d, 1H), 12.53 (s, 1H), 12.54 (s, 1H).

Analysis: Calculated for C$_{10}$H$_4$N$_2$Cl$_2$O$_2$S$_2$. 0.25 H$_2$O: C, 41.19; H, 1.56; N, 9.60; Cl, 24.31; S, 10.99%. Found: C, 41.41; H, 1.53; N, 9.38; Cl, 24.02; S, 10.97%.

EXAMPLE 8

8-Iodo[1]benzothieno[2,3-b]pyrazine-2,3(1H,4H)-dione

2-Chloro-5-nitrobenzonitrile (5.48 g, 30 mmol) was reacted with sodium sulfide and bromonitromethane following the procedure outlined in example 5 (Method J). The reaction mixture was poured onto ice-water to give a precipitate which was filtered off, washed with water and dried. Yield 6.44g (70.3%) of crude 3-amino-2,5-dinitrobenzo[b]thiophene, which had m.p. 288°-291° C. after recrystallization from alcohol. $^1$H-NMR (CDCl$_3$/DMSO-d$_6$): δ 7.8 (d, 1H), 8.38 (dd, 1H), 8.4-8.7 (br. s, 2H), 9.4 (d, 1H).

Ethoxalylation of 3-amino-2,5-dinitrobenzo[b]thiophene (15.7 g, 65.6 mmol) was performed following the procedure outlined in example 1 (Method E). Yield 21.5 g (96.6%) of ethyl N-(2,5-dinitrobenzo[b]thien-3-yl)oxamate. M.p. 178°-183° C. $^1$H-NMR (DMSO-d$_6$) <1.38 (t, 3H), 4.4 (q, 2H), 8.43 (d, 1H), 8.5 (dd, 1H), 9.08 (d, 1H), 11.8 (s, 1H).

Method L

8-amino[1]benzothieno[2,3-b]pyrazine-2,3(1H,4H)-dione hydrochloride

A suspension of ethyl N-(2,5-dinitrobenzo[b]thien-3-yl)oxamate (19.68 g, 58 mmol) in 990 ml of 80% acetic acid was stirred and flushed with a stream of dry nitrogen. Titanium trichloride (130 g, 0.84 mol) was added during 0.3 h while the temperature increased to 62° C., and the mixture was stirred 0.25 h while the temperature decreased to 35° C. The precipitate was filtered off, washed with 50 ml of 80% acetic acid and 50 ml of water and dried to give 10.0 g of crude product. By adding 2000 ml of ice-water to the filtrate another crop of 4.5 g was isolated. The crude product was triturated with alcohol (60 ml), the precipitate filtered off, washed with alcohol and dried to give 13.6 g (77%) of 8-amino[1]benzothieno[2,3-b]pyrazine-2,3(1, 1H) (1,4H)-dione, hydrochloride M.p. >300° C. $^1$H-NMR (DMSO-d$_6$): $\delta$7.3 (dd, 1H), 7.92–8.1 (2M, 2H), 9.5–11.2 (br. m, 3H), 12.6 (s, 1H), 12.75 (s, 1H).

Analysis: Calculated for $C_{10}H_8N_3ClO_2S \cdot 2H_2O$: C, 39.28%, H, 3.96%; N, 13.74%; Cl, 11.60%; S, 10.49%. Found: C, 38.97%; H, 3.45%; N, 13.33%; Cl, 11.82%; S, 10.18%.

Method M

8-Iodo[1]benzothieno[2,3-b]pyrazine-2,3(1H,4H)-dione

To a stirred suspension of 8-amino[1]benzothieno[2,-3-b]-pyrazine-2,3(1H,4H)-dione, HCl, 2H$_2$H$_2$O(1.0 g, in 15 ml of trifluoroacetic acid solid NaNO$_2$ (0,468 g, 6.78 mmol) was added during 1 h while the temperature was adjusted to 1°–5° C. The mixture was stirred for 0.5 h at 1–5° C., then KJ (1.69 g, 10.17 mmol) was added at once, and the temperature was raised to room temperature during 1 h. Stirring was continued another 2 h, and 30 ml of ice-water was added. The precipitated product was filtered off and recrystallized from DMF-water and DMF-1M HCl, triturated with boiling ethanol (60 ml) and washed with ethanol and ether to give 0.51 g (45%) of the title compound. M.p. >300° C. $^1$H-NMR (DMSO-d$_6$): 7.58 (d, 1H), 7.76 (d, 1H), 8.47 (s, 1H), 12.5 (s, 2H).

Analysis: Calculated for $C_{10}H_5N_2JO_2S$, ¼H$_2$O: C, 34.45%; H, 1.59%; N, 8.04%; S, 9.20%. Found: C, 34.17%; H, 1.68%; N, 8.22%; S, 8.84%.

EXAMPLE 9

8-Trifluoromethyl[1]benzothieno[2,3-b]pyrazine-2,3-(1H, 4H)-dione

2-Chloro-5-trifluoromethylbenzonitrile (5.0 g, 24.3 mmol) (Helv. chim. acta Vol. XLV, 2226 (1962)) was reacted with 3-mercaptopropionitrile and bromonitromethane following the procedure outlined in example 7 (Method K). Yield 2.47 g (39%) of 3-amino-2-nitro-5-trifluoromethylbenzo[b]thiophene. M.p. 198°–201° C. 1H-NMR (DMSO-d$_6$): $\delta$7.95 (d, 1H), 8.13 (d, 1H), 8.86 (s, 1H), 8.4–9.4 (br. s, 2H).

Ethoxalylation of 3-amino-2-nitro-5-trifluoromethylbenzo[b]thiophene (2.30 g, 8.77 mmol) was performed following the procedure outlined in example 1 (Method E). Yield 3.02 g (95%) of ethyl N-(2-nitro-5-trifluoromethylbenzo[]thien-3-yl)oxamate. M.p. 120°–121° C. $^1$H-NMR (DMSO-d$_6$$\delta$1.36 (t, 3H), 4.39 (q, 2H), 8.02 (d, 1H), 8.41 (d, 1H), 8.55 (s, 1H), 11.65 (s, 1H).

Method N

8-Trifluoromethyl[1]benzothieno[2,3-b]pyrazine-2,3(1H,4H)-dione

To a solution of SnCl$_2$ (0.681 g, 3.59 mmol) in 30 ml of concentrated hydrogen chloride at 65° C. was added under stirring ethyl N-(2-nitro-5- trifluoromethylbenzo[b]thien-3-yl)oxamate (0.500 g, 1.38 mmol). After 15 m additional SnCl$_2$ (0.262 g, 1.38 mmol) was added. The mixture was stirred at 65° C. for a further 45 minutes, then cooled on an ice bath, and the precipitate was filtered off, washed with water and dried to give 0.30 g (71%) of the title compound. M.p. >320° C. $^1$H-NMR (DMSO-d$_6$): $\delta$7.6 (d, 1H), 8.18 (d, 1H), 8.52 (s, 1H), 12.53 (s, 1H), 12.62 (s, 1H).

Analysis

Calculated for $C_{11}H_5N_2F_3SO_2 \cdot 1.2 H_2O$: 42.91%; H, 2.42%; N, 9.10%, S, 10.42%. Found: C, 42,63%; H, 2.32%; N, 8.80%, S, 10.43%.

EXAMPLE 10

6-Methoxy[1]benzothieno[2,3-b]pyrazine-2,3(1H,4H)-dione

A mixture of S-(2-cyano-6-methoxyphenyl)-N,N-dimethyl thiocarbamate (3.0 g, 12.7 mmol) (J. Chem. Soc. Perkin Trans. I, 2973, (1983)), 13 ml of methanol and 7.62 ml of 10% NaOH was refluxed for 3 h under a nitrogen atmosphere. The reaction mixture, containing intermediary 2-cyano-6-methoxybenzenethiolate, was cooled to 0° C. and bromonitromethane (1.5 ml, 21.6 mmol) was added dropwise. The ice bath was removed and stirring was continued for 96 h at room temperature. The precipitate was filtered off, washed with water and dried to give 1.83 g of orange crystals. Recrystallization from alkohol afforded 1.15 g (40%) of 3-amino-7-methoxy-2-nitrobenzo[b]thiophene. M.p. 255°57° C. 1H-NMR (DMSO-d$_6$): 3.96 (s, 3H), 7.25 (d, 1H), 7.45 (t, 1H), 7.94 (d, 1H), 8.90 (br. s, 2H).

A solution of 3-amino-7-methoxy-2-nitrobenzo[b]thiophene (1.12 g, 5 mmol) in 100 ml of dry THF was cooled to $-10°$ C. and flushed with a stream of dry nitrogen. Pyridine (2 ml) and 4-dimethylaminopyridine (61 mg, 0.5 mmol) was added followed by dropwise addition of a solution of ethyl oxalylchloride (1.68 ml, 15 mmol) in 10 ml of dry THF. The reaction mixture was stirred for 5 h at $-10°$ C. and 40 h at room temperature, and then poured over crushed ice. Extraction (ethyl acetate), washing, drying and evaporation afforded 1.5 g (93%) of ethyl N-(7methoxy-2-nitrobenzo[b]thien-3-yl)oxamate. M.p. 169°71° C. $^1$H-NMR (DMSO-d$_6$): $\delta$1.35 (t, 3H), 4.01 (s, 3H), 4.37(q, 2H), 7.30 (d, 1H), 7.57 (t, 3H), 7.64 (d, 1H), 11.60 (s, 1H).

Reduction of ethyl N-(7-methoxy-2-nitrobenzo[b]thien-3-yl)oxamate (1.0 g, 3.1 mmol) was performed following the procedure outlined in example 1 (Method F) to yield 0.47 g (61%) of the title compound. M.p. >300° C. $^1$H-NMR (DMSO-d$_6$): $\delta$3.94 (s, 3H), 6.93 (d, 1H), 7.40 (t, 1H), 7.66 (d, 1H), 12.43 (s, 1H), 12.56 (s, 1H).

Analysis: Calculated for $C_{11}H_8N_2O_3S \cdot 2.25 H_2O$: C, 45.75; H, 4.36; N, 9.70%. Found: C, 45,44; H, 4.08; N, 9.57%.

EXAMPLE 11

7-Methoxy[1]benzothieno[2,3-b]pyrazine-2,3(1H,4H)-dione

4-Methoxy-2-nitrobenzonitrile (18 g, 100 mmol) (L. Bradford, et al., J. Chem. Soc., 437 (1947)) was reacted with 3-mercaptopropionitrile and bromonitromethane following the procedure outlined in example 7 (Method K). Yield 6.0 g (24%) of 3-amino-6-methoxy-2-nitrobenzo[b]thiophene. M.p. >250° C. $^1$H-NMR (DMSO-d ): δ3.85 (s, 3H), 7.05 (d, 1H), 7.45 (s, 1H), 8.21 (d, 1H), 8.80 (br. s, 2H).

Ethoxalylation of 3-amino-6-methoxy-2-nitrobenzo[b]thiophene (1.3 g, 6 mmol) was performed following the procedure outlined in example 1 (Method E). Yield 1.2 g (64%) of ethyl N-(6-methoxy-2-nitrobenzo[b]thien-3-yl)oxamate. M.p. 195°-96° C. $^1$H-NMR (DMSO-d : δ1.35 (t, 3H), 3.90 (s, 3H), 4.39 (q, 2H), 7.18 (d, 1H), 7.70 (s, 1H), 7.92 (d, 2H), 11.50 (s, 1H).

Reduction of ethyl N-(6-methoxy-2-nitrobenzo[b]thien-3yl)-oxamate (0.65 g, 2 mmol) was performed following the procedure outlined in example 1 (Method F) to yield 0.3 g 61%) of the title compound. M.p. >300° C.$^1$H-NMR(DMSOd$_6$): d$_6$): δ3.80 (s, 3H), 7.05 (dd, 1H), 7.55 (d, 1H), 7.92 (d, 1H), 12.25 (br. s, 1H), 12.50 (br. s, 1H).

Analysis: Calculated for $C_{11}H_8N_2O_3$. 0.5 $H_2O$: C, 51.37; H, 3.52; N, 10.89%. Found: C, 51.09; H, 3.57; N, 10.88%;.

EXAMPLE 12

6-Chloro[1]benzothieno[2,3-b]pyrazine-2,3(1H,4H)-dione

A mixture of 2,3-dichlorobenzaldehyde (53.4 g, 305 mmol), hydroxylamine hydrochloride (31.7 g, 475 mmol), sodium formate (43.6 g, 640 mmol), and formic acid (500 ml) was heated under reflux for 6.5 h. The reaction mixture was poured into ice-water, and the precipitate was filtered off and dissolved in 500 ml of dichloromethane. Drying (MgSO$_4$) and evaporation afforded 34 g (65%) of 2,3-dichlorobenzointrile, M.p. 49°-50° C. $^1$H-NMR (CDCl$_3$): δ7.32 (t, 1H), 7.61 (dd, 1H), 7.70 (dd, 1H).

2,3-Dichlorobenzonitrile (4.2 g, 25 mmol) was reacted with 3-mercaptopropionitrile and bromonitromethane following the procedure outlined in example 7 (Method K) to afford 3.9 q (71%) of 3-amino-7-2-nitrobenzo[b]thiophene. M.p. >250° C. $^1$H-NMR (DMSO-d$_6$): δ7.56 (t, 1H), 7.81 (d, 1H), 8.32 (d, 1H), 9.10 (br. s, 2H).

Ethoxalylation of 3-amino-7-chloro-2-nitrobenzo[b]thiophene (1.0 g, 5 mmol) was performed following the procedure outlined in example 1 (Method E) to afford 0.8 g (54%) of ethyl N-(7-chloro-2-nitrobenzo[b]thien-3-yl)oxanate. $^1$H-NMR (DMSO-d$_6$): δ1.38 (t, 3H), 4.39 (q, 2H), 7.68 (t, 1H), 7.90 (d, 1H), 8.11 (d, 1H), 11.70 (s, 1H).

Reduction of ethyl N-(7-chloro-2-nitrobenzo[b]thien-3yl)oxamate (0.2 g, 0.6 mmol) was performed following the procedure outlined in example 1 (Method F) to yield 0.04 g (25%) of the title compound. M.p. >300° C. $^1$H-NMR (DMSO-d$_6$): δ7.38 (d, 1H), 7.46 (t, 1H), 7.98 (d, 1H), 12.51 (s, 1H), 12.60 (s, 1H).

Analysis: Calculated for $C_{10}H_5N_2Cl0_2S$. $H_2O$: C, 44.37; H, 2.60; N, 10.34%. Found: C, 44.16; H, 2.70; N, 9.81%.

EXAMPLE 13

6-Fluoro[1]benzothieno[2,3-b]pyrazine-2,3(1H,4H)-dione 2,3-difluorobenzonitrile (5.0 g, 35.9 mmol) was reacted with 3-mercaptopropionitrile and bromonitromethane following the procedure outlined in example 7 (Method K). Yield 4.72 g (62%) of 3-amino-2-nitro-7-fluorobenzo[b]thiophene. M.p. 238°-40° C. $^1$H-NMR (DMSO-d$_6$): δ7.48-7.65 (m, 2H), 8.21 (d, 1H), 8.65-10.3 (br. s, 2H).

Ethoxalylation of 3-amino-2-nitro-7-fluorobenzo[b]thiophene (4.5 g, 21.21 mmol) was performed following the procedure outlined in example 1 (Method E). Yield 5.93 g (89.5%) of ethyl N-(2-nitro-7-fluorobenzo[b]thien-3-yl)oxamate. M.p. 148°-151° C. $^1$H-NMR (DMSO-d$_6$): δ1.37 (t, 3H), 4.40 (q, 2H), 7.66 (m, 2H), 7.96 (m, 1H), 11.72 (s, 1H).

Reduction of ethyl N-(2-nitro-7-fluorobenzo[b]thien-3-yl)oxamate (2.5 g, 8.0 mmol) was performed following the procedure outlined in example 9 (Method N) to yield 1.05 g (55.6%) of the crude title compound. Purification was performed by recrystallization from acetic acid, and trituration of the substance with alcohol and water. M.p. >35° C. $^1$H-NMR (DMSO-d$_6$) δ7.21 (m, 1H), 7.47 (m, 1H), 7.88 (m, 1H), 12.5 (s, 1H), 12.65 (s, 1H).

Analysis: Calculated for $C_{10}H_5N_2FO_2S$: C, 50.86; H, 2.13; N, 11.85; S, 13.57%. Found: C, 50.39; H, 2.17; N, 11.53; S, 13.14%.

EXAMPLE 14

7-Bromo-8-fluoro[1]benzothieno[2,3-b]pyrazine-2,3-(1H,4H)-dione

A mixture of 7-fluoro[1]benzothieno[2,3-b]pyrazine-2,3(1H,4H)-diom hydrate (0.3 g, 1.18 mmol), bromine (0.283 g, 1.77 mmol) and glacial acetic acid (100 ml) was heated at 95°100° C. for 2.5 h. The reaction mixture was cooled to room temperature and the precipitate was filtered off, washed with glacial acetic acid (10 ml), and dried at 110° C. for 20 h to afford 0.18 g (49%) of the title compound. M.p. >300° C. $^1$H-NMR (DMSO-d6): δ. 7 96 (d, 1H), 8.37 (d, 1H), 12.45 (br. s, 2H). Analysis: Calculated for $C_{10}H_4N_2BrFO_2S$: C, 38.12; H, 1.28; N, 8.89; Br, 25.36; S, 10.17%. Found: C, 38.00; H, 1.33; N, 8.76; Br, 25.38; S, 10.28%.

We claim:

1. A compound of formula (I)

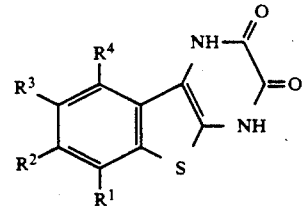

wherein
R$^1$, R$^2$, R$^3$ and R$^4$ independently are hydrogen, halogen, C$_{1-6}$-alkyl, C$_{1-6}$-alkoxy or trifluoromethyl; or a pharmaceutically acceptable salt thereof.

2. A compound which is 8-fluoro[1]benzothieno [2,3-b]pyrazine-2,3(1H, 4H)dione; 8-chloro[1]benzothieno[2,3-b]pyrazine-2,3(1H, 4H)-dione; 8-bromo[1]benzothieno[2,3-b]pyrzine-2,3(1H, 4H)-dione; 6- chloro[1]benzothieno[2,3-b]pyrazine-2,3(1H, 4H)-dione; 6fluoro[1]benzothieno[2,3-b]pyrzzine-2,3(1H, 4H)-dione; or a pharmaceutically acceptable salt thereof.

3. A pharmaceutical composition fo ruse in treating epilepsy, convulsions, anxiety or ischemia comprising an effective amount of a compound according to claim 1 together with a pharmaceutically acceptable carrier or diluent.

4. The pharmaceutical composition according to claim 3 in the form of an oral dosage unit contianing about 1-200 mg of the compound.

5. A method of treating epilepsy, convulsions, anxiety or ischemia in a subject in need thereof comprising administering an effective of a compound according to claim 1.

6. A method of treating epilepsy, convulsions, anxiety or ischemia in a subject in need thereof comprising administering a pharmaceutical composition according to claim 3.

* * * * *